United States Patent [19]

Schnell

[11] 4,293,413

[45] Oct. 6, 1981

[54] DIALYZER BLOOD CIRCUIT AND BUBBLE TRAPS

[75] Inventor: William J. Schnell, Wheeling, Ill.

[73] Assignee: Baxter Travenol Laboratories, Inc., Deerfield, Ill.

[21] Appl. No.: 108,118

[22] Filed: Dec. 28, 1979

[51] Int. Cl.$^3$ .............................................. B01D 31/00
[52] U.S. Cl. .................................. 210/188; 210/321.3
[58] Field of Search .............. 165/158; 210/22, 321 B, 210/188, 425; 55/52, 190

[56] References Cited

U.S. PATENT DOCUMENTS

| 250,868 | 12/1881 | Abbott | 210/425 |
|---|---|---|---|
| 4,038,190 | 7/1977 | Baudet et al. | 264/258 X |
| 4,047,563 | 9/1977 | Kurata | 165/158 |
| 4,151,088 | 4/1979 | Wolf, Jr. et al. | 210/188 X |

*Primary Examiner*—Frank A. Spear, Jr.
*Attorney, Agent, or Firm*—Paul C. Flattery; Garrettson Ellis

[57] ABSTRACT

A blood dialyzer system which comprises a membrane dialyzer carried by dialysis solution delivery means and having blood and dialysis solution inlets and outlets. The membrane dialyzer is carried in a position whereby the blood inlet is vertically lower than the blood outlet, and the dialysis solution outlet is vertically lower than the dialysis solution inlet. Bubble trap means are provided in direct communication with the blood outlet and blood flow conduits, with the bubble trap means being preferably attached to and carried by the membrane dialyzer. The dialysis solution delivery means is adapted to permit intermittent reversal of the normal flow of dialysis solution through the membrane dialyzer to remove air bubbles trapped therein. Also, improved designs of integral bubble traps carried by dialyzers are shown.

7 Claims, 3 Drawing Figures

DIALYZER BLOOD CIRCUIT AND BUBBLE TRAPS

BACKGROUND OF THE INVENTION

In the typical commercial dialyzer arrangement, particularly in the case of hollow fiber-type dialyzers positioned in a tubular housing, the dialysis solution inlet is positioned vertically lower than the dialysis solution outlet of the dialyzer. Correspondingly, in the case of hollow fiber dialyzers, this requires, for the optimum counterflow arrangement, that the blood inlet be positioned vertically higher than the blood outlet.

The reason for the above arrangement is that the bubbles which may pass into the dialyzer through the dialysis solution flow path can be swept out of the dialyzer in a much more effective manner if the dialysis solution outlet is positioned vertically above the inlet. In the opposite circumstance, bubbles may collect in the dialysis solution flow path, which interferes with the dialysis efficiency of the device.

In this conventional circumstance, where the blood flows downwardly, typical dialysis arrangements have called for an upstream bubble trap in the blood flow line, to keep air out of the blood flow path of the dialyzer, to avoid air blocking of the membrane flow channels, which can take place because of the natural buoyancy of air, which tends to try to rise against the downwardly-flowing current of the blood.

Also, a downstream bubble trap must be provided in the blood flow circuit of the dialysis system for safety, since it is imperative to avoid the infusion of air bubbles to the patient.

In accordance with this invention, an improved dialysis system is provided which permits the elimination of one of the bubble traps in the blood flow circuit, which of course results in a significant cost savings in each dialysis procedure.

The invention of this application takes advantage of improved dialysis delivery system techniques to permit the simplification of the dialysis system resulting from a downward flow path of the dialysis solution through the dialyzer.

Furthermore, the system of this invention may be simplified for the user by providing a bubble trap which is integral with the dialyzer unit, carried at the outlet of the blood flow path from the dialyzer, for greater ease of setup by the user.

DESCRIPTION OF THE INVENTION

In accordance with this invention, a blood dialyzer, or any other type of membrane diffusion device, is provided which comprises a membrane dialyzer carried by dialysis solution delivery means. The membrane dialyzer defines a blood inlet and outlet communicating with a blood flow conduit, and also defines a dialysis solution inlet and outlet communicating through solution flow conduit means with the dialysis solution delivery means.

The membrane dialyzer is carried in a position whereby the blood inlet is vertically lower than the blood outlet, and the dialysis solution outlet is vertically lower than the dialysis solution inlet.

Bubble trap means may be provided in direct communication with the blood outlet and flow conduit, with the bubble trap means being preferably attached to and carried by the membrane dialyzer.

The dialysis solution delivery means is adapted to intermittently, as needed, reverse the normal flow of dialysis solution through the membrane dialyzer, to remove air bubbles trapped in the membrane dialyzer.

Preferably, this invention is used with membrane dialyzers which are of the countercurrent flow type, for example, the commercially available capillary fiber dialyzers such as the CF ® dialyzers sold by the Artificial Organs Division of Travenol Laboratories, Inc., or plate type dialyzers.

Furthermore, the dialyzer of this invention may carry bubble trap means in direct communication with the outlet of the blood flow path, with the bubble trap means comprising a hollow housing member in the shape of a truncated cone having a wide end and a narrow end, sealed to the dialyzer at the wide end with the communicating blood outlet end being positioned centrally therein. Outlet port means may be provided in the wall of the bubble trap housing and preferably positioned in the half of the housing wall which is adjacent to the wide end, and most preferably closely adjacent to the wide end.

Upstanding baffle means may be positioned longitudinally within the hollow housing of the bubble trap, and positioned in front of the outlet port means, but spaced therefrom, to prevent the direct flow of blood from the outlet end of the blood flow path of the dialyzer to the outlet port means. Means may also be provided for the aseptic removal of collected bubbles positioned adjacent to the narrow end of the hollow housing member. This means typically may be a needle-piercable injection site.

In the drawings, FIG. 1 is an elevational view of a blood dialyzer system in which a membrane dialyzer is shown to be attached to a dialysis solution delivery means or machine.

Figure 1:
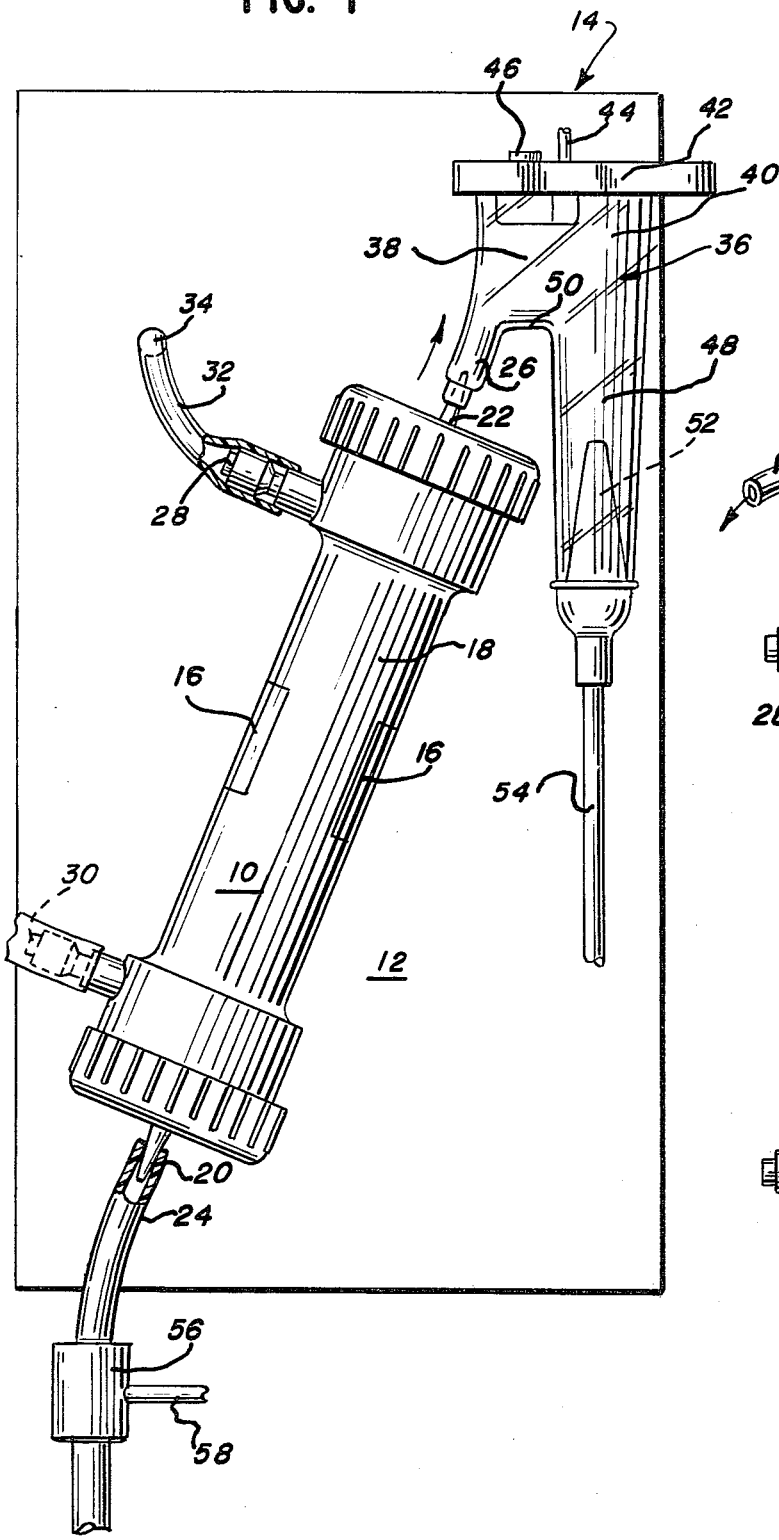
Figure 2:
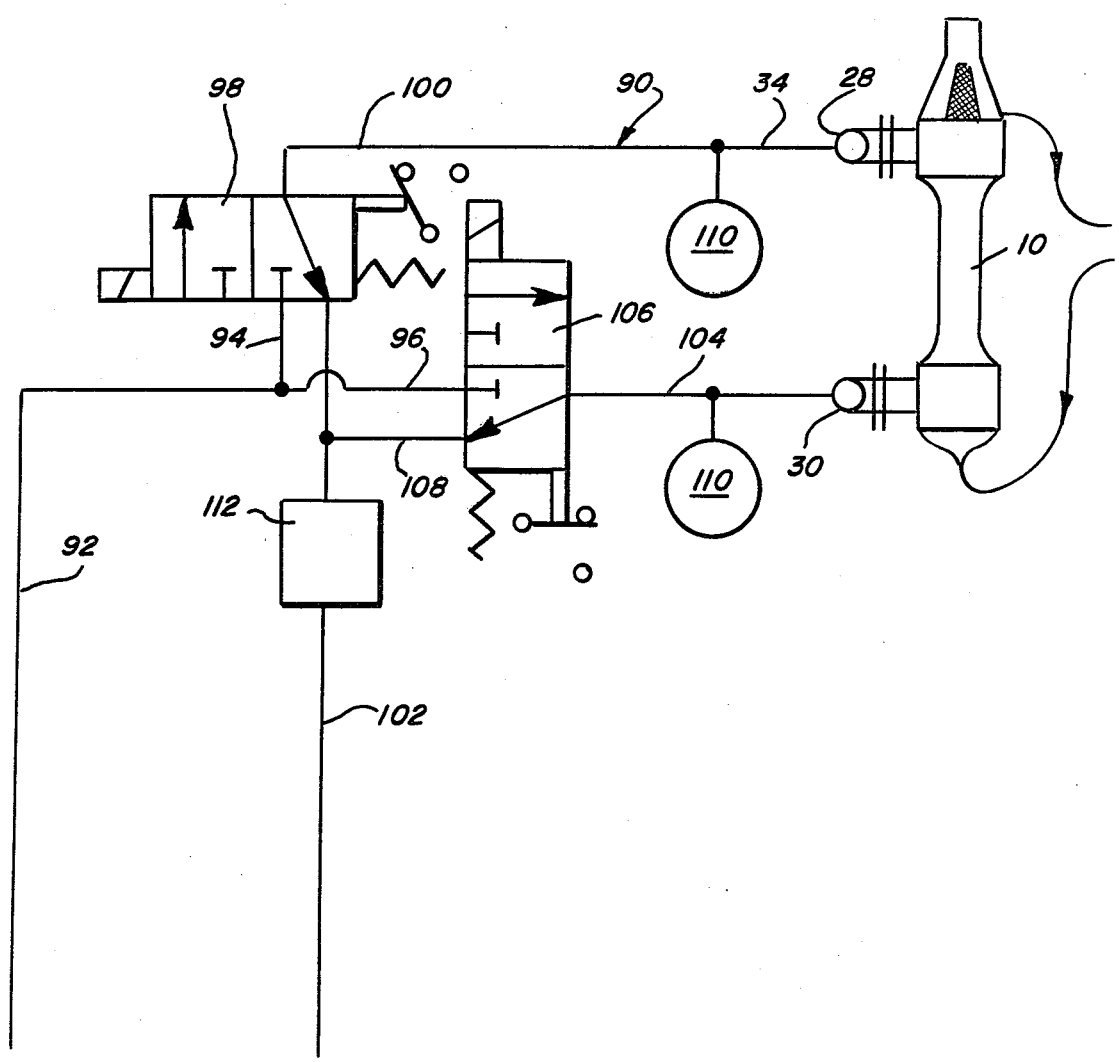
FIG. 2 is a schematic diagram showing one mode of operation of a flow reversal system for the dialysis solution delivery means shown in this invention.

Referring to FIGS. 1 and 2, a blood dialyzer system is provided which comprises a membrane dialyzer 10 which is specifically shown to be a conventional capillary fiber dialyzer similar to the CF ® dialyzer sold by the Artificial Organs Division of Travenol Laboratories, Inc., attached to the housing 12 of a dialysis solution delivery system 14 by conventional means, for example, a resilient C-clamp 16 proportioned to allow the snap-fit of housing 18 of membrane dialyzer 10.

As shown, membrane dialyzer 10 defines a blood inlet 20 and a blood outlet 22 communicating with blood flow conduit 24, 26.

Membrane dialyzer 10 also defines a dialysis solution inlet 28 and outlet 30, with dialysis solution inlet 28 receiving dialysis solution through line 32 from a solution outlet 34 in the dialysis solution delivery means 14. The dialysis solution may be mixed from concentrate, brought to the proper temperature, and debubbled by the dialysis solution delivery system 14.

As can be seen from FIG. 1, membrane dialyzer 10 is carried in a position whereby blood inlet 20 is vertically lower than blood outlet 22. Correspondingly, the dialysis solution outlet 30 is vertically lower than the dialysis solution inlet. Accordingly, any bubbles which are present in the blood entering dialyzer 10 through inlet 20 will tend not to be trapped but to pass upwardly out of port 22. On the other hand, any bubbles which enter the dialysis solution compartment of dialyzer 10 through inlet 28 may have a tendency to be trapped within the dialyzer, since the flow of dialysis solution is downward.

Because of the upward flow of the blood to the dialyzer, it no longer is necessary to have a bubble trap positioned upstream of dialyzer 10 in communication with blood flow conduit 24, which results in a clear cost saving with respect to the disposable equipment used herein, i.e., the dialyzer 10 and its blood flow circuitry.

Membrane dialyzer 10 carries a bubble trap 36 preferably attached to the membrane dialyzer, as shown. Conduit 26 may be permanently sealed to outlet port 22. Bubble trap 36 comprises flexible conduit 26 for the inlet of blood, which may preferably be integral with a flexible plastic bubble trap housing 38, which may be made out of polyvinyl chloride plastic or the like.

Housing 38, as shown, defines a tubular, relatively enlarged upper portion 40, which is closed by a cap 42, which contains a conventional pressure monitor line 44 communicating with the interior of the bubble trap, most of which is broken away for purposes of clarity of disclosure. Also, a conventional needle access port 46, normally sealed with a latex diaphragm or the like, may be provided for sampling of the blood.

The lower portion 48 of flexible housing 38 defines a tubular portion of reduced transverse dimension compared with the upper portion 40, with the junction between upper portion 40 and lower portion 48 being abruptly defined by a step wall portion 50.

In the lower end of lower portion 48, a conventional blood filter 52 may be provided which is sealed to the inner periphery of lower portion 48, and a sealed blood outlet tube 54 to convey the debubbled blood back to the arterial system of the patient.

The overall design of the bubble trap may be as disclosed in the copending U.S. application Ser. No. 907,363, filed May 18, 1978, of Marc Bellotti, et al. entitled "MEDICAL SET FOR A DIFFUSION DEVICE".

As described below with respect to FIG. 2, any conventional dialysis solution delivery system 14, capable of delivering generally bubble-free dialysis solution to inlet 28 of dialyzer 10, is provided. Even if some bubbles do form and are trapped in the dialyzer, the dialysis solution delivery system 14 is preferably capable of reverse dialysis solution flow by means shown in FIG. 2, so that the bubbles may be removed from dialyzer 10 and sucked back into the delivery system 14 through outlet 34, where the dialysis solution and bubbles may be shunted to a drain. After this, the flow is reversed again to its normal direction, and fresh, bubble-free dialysis solution will once again pass through the dialyzer between inlet 28 and outlet 30.

Blood passes, typically from the venous system of a patient, via conduit 24, which may be part of a venous set, through inlet 20 and outlet 22 of dialyzer 10, being dialyzed in conventional manner against the counterflowing dialysis solution. Thereafter, blood enters conduit 26, which may be part of an arterial set, with a substantial upward flow component into bubble trap 36, where the upward flow component impels bubbles in the blood upwardly above the blood level in housing 38. Blood is withdrawn from the bottom of lower portion 48, where the flow is relatively quiescent and free of bubbles, so that the blood withdrawn through line 54 for return to the arterial system of the patient is bubble-free.

As shown in FIG. 1, the longitudinal axis of the main flow path through dialyzer 10 preferably occupies an angle of about 20° to 60° from the vertical so that the dialysis solution inlet 28 and outlet 30 point upwardly to some extent. This significantly facilitates the removal of air from dialyzer 10 during the priming procedure, and also in the event that air bubbles must be removed from the dialysate compartment by reverse operation of dialysis solution delivery system 14.

Conduit 26 may also define about a 20° to 60° angle from the axis of lower portion 48.

As the result of the above improvement, a dialyzer unit is provided having an integrally carried bubble trap communicating with the blood outlet from the dialyzer. This provides substantial convenience of assembly, with the entire arterial set of the dialyzer system being optionally integral with the dialyzer 10 and bubble trap 36. If desired, the venous set exemplified by conduit 24 may also be integrally attached to dialyzer 10 if desired. This assures proper assembly of the apparatus, and places less burden upon the user to provide sterile connection of the various set components. At the same time, the venous set exemplified by conduit 24 can be greatly simplified and reduced in cost, since the need for the venous set bubble trap is dispensed with.

Conduit 24 comprising a portion of the venous set may include other conventional components of such a set, specifically, a T-connection member 56 and a pressure monitor line 58, of which may communicate with a conventional pressure monitoring apparatus.

Referring to FIG. 2, the flow reversing system 90 is shown, which may be part of dialysis solution delivery system 14 and positioned within or carried by housing 12. The remaining components of dialysis solution delivery system 14 may be of any conventional design. Various dialysis solution delivery systems are commercially available at the present time.

Dialysis solution inlet line 92 leads from the conventional portion of the dialysis solution delivery system 14, line 92 being provided with a supply of degassed dialysis solution having a proper concentration of solutes, and maintained at the proper temperature.

Line 92 divided into a pair of branched lines 94, 96. Line 94 leads to a three-way flow reversing solenoid valve 98, a type of which is commercially available, for example, from Skinner Precision Industries, Inc., of New Britain, Conn. Valve 98 also communicates with dialysis solution inlet line 100 which, in turn, communicates through aperture 34 to dialysis solution inlet 28 of dialyzer 10.

Valve 98 also communicates with drain line 102, with valve 98 being mechanically operable to alternatively connect lines 94 and 100 while closing line 102 and lines 102 and 100 while closing line 94.

Dialysis solution passing out of outlet 30 enters flow line 104 which, in turn, communicates with three-way reversing solenoid valve 106, which may be of similar design to valve 98. Valve 106 is capable of alternatively providing communication between branch line 96 and line 104 while blocking flow through connector line 108, which, in turn, communicates with drain line 102. Alternatively, valve 106 can provide connection between lines 104 and 108 while blocking line 96.

Pressure monitors 110 may be connected to lines 100 and 104, and blood leak detector 112 may be provided in drain line 102.

Accordingly, dialysis solution passing through line 92 may, in the normal operating condition of valves 98, 106, pass through valve 98 into line 100, and from there through the dialyzer 10. Spent dialysis solution exits from dialyzer 10 into line 104, where it normally passes through valve 106 and line 108 to the drain line 102.

However, in the event that a temporary reversed flow of dialysis solution is desired to assist in priming, or to remove bubbles from dialyzer 10, both valves 98, 106 are moved to their alternate flow positions. Accordingly, dialysis solution passing through line 92 is blocked from passage through line 94, but does pass through line 96 and valve 106 into line 104, and thus into the dialyzer in reversed flow pattern.

The dialysis solution then exits from dialyzer 10 into line 100, where it passes through valve 98 into drain line 102.

Figure 3:
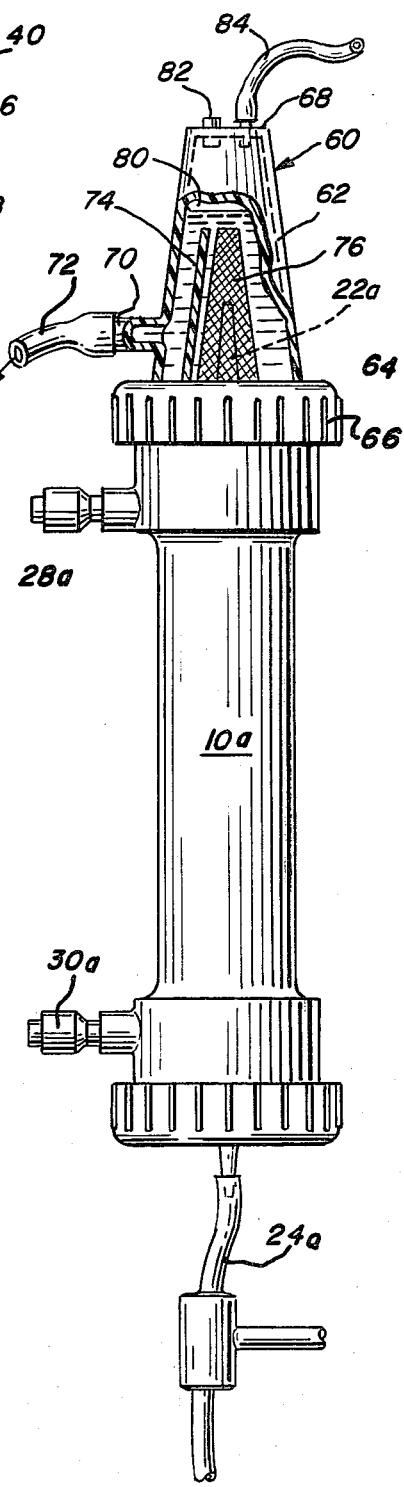
FIG. 3 is an elevational view of an alternate embodiment of the membrane dialyzer, suitable for mounting on the dialysis delivery means, and carrying another design of bubble trap.

Referring to FIG. 3, a modification of the dialyzer and bubble trap system of FIG. 1 is shown, which modification may be attached to dialysis solution delivery system 14 and used in the manner described above.

Membrane dialyzer 10a is shown, which may be similar in design to membrane dialyzer 10 except for the design of bubble trap used. Blood inlet conduit 24a may constitute a venous set of design similar to the previous conduit 24. The dialysis solution inlet 28a and outlet 30a are also used in the same manner.

Blood outlet 22a is surrounded by bubble trap 60. Bubble trap 60 comprises a hollow housing member 62, which may be in the shape of a truncated cone having a wide end 64, which is sealed to end cap 66 of dialyzer 10a. End cap 66 may otherwise be of conventional design.

Housing 62 also defined a narrow end 68. Blood outlet port means 70, which may be connected to conduit 72 constituting part of an arterial set, is positioned in the wall of housing 62 as shown. Upstanding baffle means 74 is positioned longitudinally within the hollow housing member 62, and positioned in front of the outlet port 70 relative to blood outlet 22a. Baffle 74 is spaced as well from outlet port means 70, and has the function of preventing the direct flow of blood from the outlet 22a to the outlet port means 70.

Blood filter 76 is provided as well, carried by end cap 66.

Accordingly, any bubbles which are present in the blood passing out of port 22a are impelled upwardly, along with the general flow of the blood, to join the gas pocket 80 at the upper part of housing 62. Outlet port 70, which is preferably positioned in the half of the housing member wall which is adjacent to lower, wide end 64, withdraws blood from lower portions of the blood supply in the bubble trap 60.

A conventional needle-piercable access port 82 may be provided for removal of gases from time to time from bubble 80 as may be necessary. Conduit 84 communicates with the interior of bubble trap 60, and provides access for a pressure monitor device.

The above has been offered for illustrative purposes only, and is not intended to limit the invention of this application, which is as defined in the claims below.

That which is claimed is:

1. A blood dialyzer system which comprises a membrane dialyzer carried by dialysis solution delivery means, said membrane dialyzer defining a blood inlet and outlet communicating with blood flow conduits, and also defining a dialysis solution inlet and outlet communicating through solution flow conduit means with said dialysis solution delivery means, said membrane dialyzer being carried in a position whereby said blood inlet is vertically lower than said blood outlet, and said dialysis solution outlet is vertically lower than said dialysis solution inlet, and bubble trap means in direct communication with said blood outlet and blood flow conduits, said bubble trap means being attached to and carried by said membrane dialyzer, said dialysis solution delivery means being adapted to intermittently reverse the normal flow of dialysis solution through said membrane dialyzer to remove air bubbles trapped in said membrane dialyzer.

2. The blood dialyzer system of claim 1 in which said membrane dialyzer is of the countercurrent flow type.

3. The blood dialyzer system of claim 2 in which the axis of the main dialysate flow path in the membrane dialyzer occupies an angle of 20° to 60° with the vertical, with said dialysis solution inlet and outlet pointing upwardly from the horizontal.

4. The blood dialyzer system of claim 3 in which said bubble trap means comprises a distinct, enlarged chamber area at an upper portion thereof connected by a step wall to a lower portion thereof which is not transversely enlarged, and a conduit for receiving blood from said blood outlet spaced from the bottom of said chamber and communicating directly with said enlarged upper chamber portion in an upwardly-pointing direction through said step wall, an outlet positioned adjacent the end of said lower portion remote from said enlarged, upper portion of said chamber, and vent means for gases being positioned at the upper end of said receiving chamber.

5. The blood dialyzer system of claim 4 in which blood filter means is positioned in the lower portion of said chamber.

6. The blood dialyzer system of claim 2 in which said bubble trap means comprises a hollow housing member in the shape of a truncated cone having a wide end and a narrow end, sealed to said dialyzer at said wide end with said communicating blood outlet positioned centrally therein, outlet port means in the wall of said housing member, upstanding baffle means positioned longitudinally within said hollow housing member and positioned in front of said outlet port means but spaced therefrom, to prevent the direct flow of blood from said outlet and to the outlet port means, and means for the aseptic removal of collected bubbles positioned adjacent the narrow end of said hollow housing member.

7. The blood dialyzer system of claim 6 in which the outlet port means is positioned in the half of the housing member wall which is adjacent to said wide end.

* * * * *